United States Patent [19]

Collins et al.

[11] 4,087,447

[45] May 2, 1978

[54] ANTI-SECRETORY PROSTAGLANDINS INTERMEDIATES

[75] Inventors: Paul W. Collins, Deerfield; Raphael Pappo, Skokie, both of Ill.

[73] Assignee: G. D. Searle & Co., Chicago, Ill.

[21] Appl. No.: 770,537

[22] Filed: Feb. 22, 1977

[51] Int. Cl.² .............................................. C07F 7/22
[52] U.S. Cl. ............................. 260/429.7; 542/413; 542/426; 560/121
[58] Field of Search ...................... 260/429.7

[56] References Cited

U.S. PATENT DOCUMENTS 4,038,308  7/1977  Strike ........................... 260/429.7 X

OTHER PUBLICATIONS

Corey, et al., J.A.C.S., 98(1), pp. 222-224 (1976).
Chemical Abstracts, 82 125452y (1975).
Chemical Abstracts, 84 31199k (1976).
J. Organometallic Chem. 109 267,288,328 (1976).
J. Organometallic Chem. 53 30-32 (1973).

*Primary Examiner*—Helen M. S. Sneed
*Attorney, Agent, or Firm*—John J. McDonnell

[57] ABSTRACT

The present invention encompasses novel intermediates of the formula:

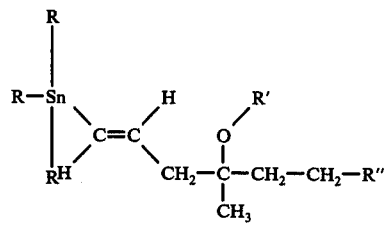

wherein R is phenyl, cyclohexyl or lower alkyl having 1–6 carbon atoms; R' is trialkylsilyl wherein the alkyls have 1–4 carbon atoms, tetrahydropyran-2-yl, or tetrahydrofuran-2-yl; and R" is lower alkyl having 1 to 3 carbon atoms. Compounds of the present invention are useful in synthesizing prostaglandin-like molecules which are active anti-secretory agents.

4 Claims, No Drawings

ANTI-SECRETORY PROSTAGLANDINS INTERMEDIATES

The present invention encompasses novel intermediates of the formula:

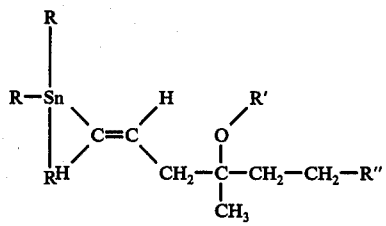

wherein R is phenyl, cyclohexyl or lower alkyl having 1-6 carbon atoms; R' is trialkylsilyl wherein the alkyls have 1-4 carbon atoms, tetrahydropyran-2-yl, or tetrahydrofuran-2-yl; and R" is lower alkyl having 1 to 3 carbon atoms. Compounds of the present invention are useful in synthesizing prostaglandin-like molecules which are active anti-secretory agents.

Thus, R represents methyl, ethyl, propyl, butyl, pentyl, cyclohexyl, hexyl and phenyl; and R" represents methyl, ethyl or propyl.

Preferred embodiments of the present invention are compounds of the formula:

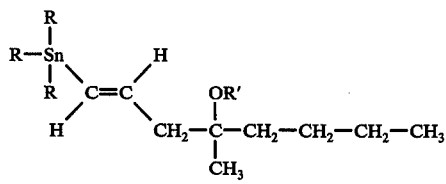

wherein R and R' are as previously defined. Especially preferred are embodiments where R is n-butyl.

Compounds of the present invention are prepared by the light or free radical catalysed addition of a corresponding tin hydride to the substituted acetylene as shown in Scheme I. The intermediate is converted to active prostaglandins by Route A or B.

SCHEME 1

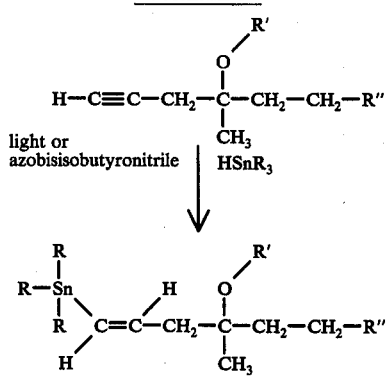

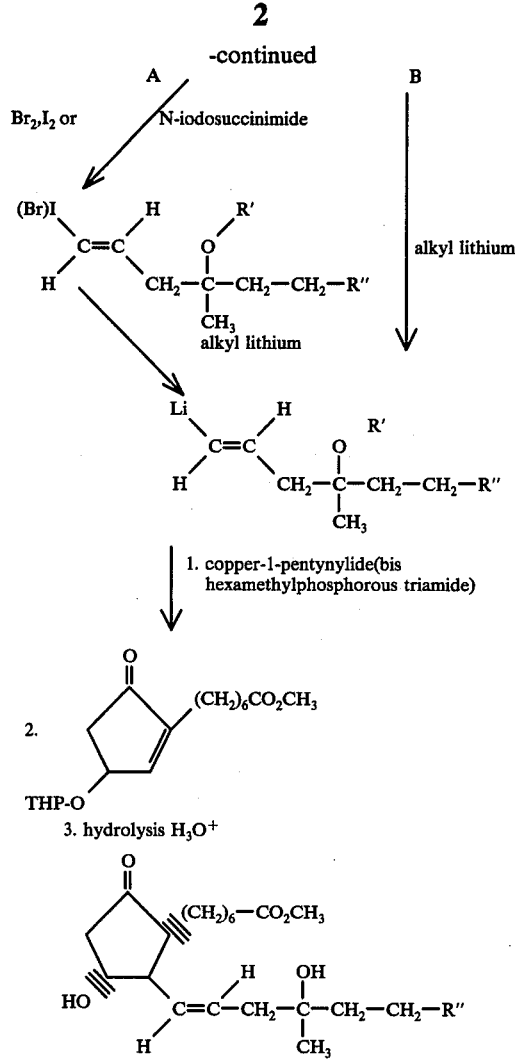

Corey et al., J. Am. Chem. Soc. 98, 223 (1976) describes compounds of the formula:

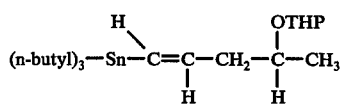

THP = tetrahydropyran

Compounds of the present invention are particularly distinct in that they are derived from tertiary alcohols wherein hydrogen is replaced with propyl, butyl, or pentyl.

Compounds of the present invention are intermediates for the preparation of prostaglandin-like compounds which display valuable pharmacological properties as is exemplified by their ability to inhibit the gastric secretion stimulated by secretogogues such as histamine and pentagastrin.

The specific assay used to detect gastric anti-secretory activity is described as follows:

Adult female beagle dogs weighing 13–20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg/hr. The volume of the diffusion is kept at approximately 13 ml/hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

The compounds prepared from intermediates of the present invention are combined with common pharmaceutical carriers and administered to animals in need of anti-secretory treatment. For example, propantheline bromide described in Cuttings Handbook of Pharmacology, 4th edition, Appleton-Century-Crofts, N.Y., N.Y., page 548 is active in the above test.

The invention will appear more fully from the examples which follow. The examples are given by way of illustration only and are not to be construed as limiting the invention either in spirit or in scope as many modifications both in materials and methods will be apparent to those skilled in the art. In these examples temperatures are given in degrees centigrade (° C.) and quantities of materials in parts by weight unless otherwise noted.

EXAMPLE 1

2.12 Parts of 4-methyl-1-octyn-4(RS)ol trimethylsilyl ether is mixed neat with 2.91 parts of tri-n-butyltin hydride and stirred in an inert atmosphere at 0° C in the presence of ultraviolet light for 1-2 hours to provide 4-methyl-4(RS)-trimethylsilyloxy oct-trans-1-enyl tri-n-butyltin, having the formula

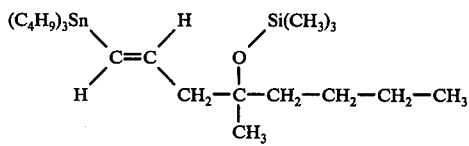

Alternately, 0.1 part of azobisisobutyronitrile is added to the neat mixture and heated at 80°–90° for 2–3 hours to provide the same product.

5.03 Parts of the vinyl tin compound are dissolved in 25 parts by volume of anhydrous tetrahydrofuran and cooled to −40° C under nitrogen and treated with 4 parts by volume of 2.5 molar n-butyl lithium. The solution is stirred at −40° C for 1 hour and −30° C for 30 minutes.

The reaction mixture is cooled to −60° C and a solution of 4.5 parts of copper 1-pentynylide bis-hexamethylphosphorous triamide (prepared from 1.30 parts of copper pentynylide and 3.20 parts of hexamethyl phosphorous triamide) in 18 parts by volume of ether is added and the resulting solution is stirred at −60° C for 15 minutes.

1.28 Parts of methyl 7-[3(RS)tetrahydropyran-2-yloxy-5-oxocyclopent-1-ene]heptanoate dissolved in 8 parts by volume of ethyl ether is added to the above copper reagent. The reaction mixture is stirred at −45° C for 1½ hours. The reaction mixture is then partitioned between ether and cold dilute hydrochloric acid. The ether layer is separated, diluted with approximately 500 parts by volume of an ether-ethyl acetate mixture, washed once with water, filtered, dried over anhydrous sodium sulfate, and stripped of solvent by distillation under reduced pressure. The resulting residue is purified by chromatography on a silica gel column, using a 30:70 mixture of ethyl acetate and benzene as the eluent. Removal of the solvent from the eluent affords pure racemic methyl 7-[(3(α)-tetrahydropyran-2-yloxy)-2β-(4(RS)-4-methyl-4-trimethylsilyloxy-trans-1-octen-1-yl)-5-oxocyclopent-1α-yl]heptanoate.

A solution consisting of 0.85 part of the latter compound dissolved in 50 parts by volume of a 3:1:1 acetic acid:water:tetrahydrofuran mixture is allowed to stand at room temperature for about 16 hours. The reaction mixture is diluted with ether and is washed several times with water, dried over anhydrous sodium sulfate, stripped of solvent under reduced pressure and purified by chromatography using 100% ethyl acetate as eluent. Removal of the solvent from the eluent affords pure racemic methyl 7-[3(α)-hydroxy-2β-(4(RS)-4-hydroxy-4-methyl-trans-1-octen-1-yl)-5-oxocyclopent-1α-yl]heptanoate. This compound is represented by the following structural formula:

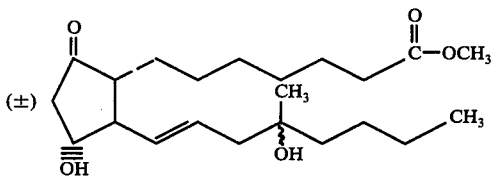

EXAMPLE 2

Following the procedure in Example 1 using wherein the hydroxyl is protected with triethylsilyl, tetrahydropyran-2-yl, or tetrahydrofuran-2-yl respectively provides:

4-methyl-4(RS)-triethylsilyloxy oct-trans-1-enyl tri n-butyltin, 4-methyl-4(RS)-tetrahydropyran-2-yloxy oct-trans-1-enyl -tri n-butyltin, and 4-methyl-4(RS)-tetrahydrofuran-2-yloxy oct-trans-1-enyl -tri n-butyltin.

In a similar manner, replacing tri n-butyltin hydride with triphenyltin hydride, provides 4-methyl-4(RS)-trimethylsilyloxy oct-trans-1-enyl triphenyltin and replacement with tri n-hexyltin hydride provides 4-methyl-4(RS)-trimethylsilyloxy oct-trans-1-enyl tri n-hexyltin.

Likewise replacing tri-n-butyltin hydride with tricyclohexyl tin hydride provides 4-methyl-4(RS)-trimethylsilyloxy oct-trans-1-enyl tricyclohexyltin.

Also following the procedure of Example 1 all of these intermediates are converted to the prostaglandin of Example 1.

EXAMPLE 3

Following the procedure of Example 1, 4-methyl-1-heptyn-4(RS)-ol trimethylsilyl ether is converted to racemic methyl 7-[3α-hydroxy-2β-(4(RS)-4-hydroxy-4-methyl-1-hepten-1-yl)-5-oxocyclopent-1α-yl]heptanoate having the following structural formula:

What is claimed is:

1. A compound of the formula:

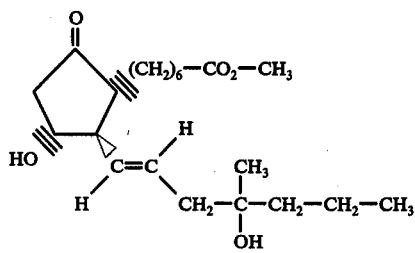

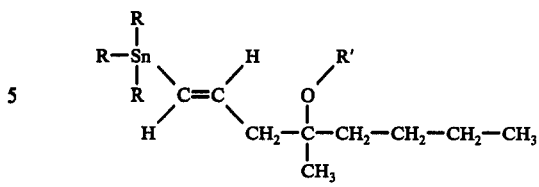

wherein R is lower alkyl having 1–6 carbon atoms and R' is trialkylsilyl wherein the alkyls have 1–4 carbon atoms.

2. A compound according to claim 1 which is 4-methyl-4(RS)-trimethylsilyloxy oct-trans-1-enyl tri-n-butyltin.

3. A compound according to claim 1 which is 4-methyl-4(RS)-triethylsilyloxy oct-trans-1-enyl tri-n-butyltin.

4. A compound according to claim 1 which is 4-methyl-4(RS)-trimethylsilyloxy oct-trans-1-enyl tri n-hexyltin.

* * * * *

Notice of Adverse Decision in Interference

In Interference No. 100,359, involving Patent No. 4,087,447, P. W. Collins and R. Pappo, ANTI-SECRETORY PROSTAGLANDINS INTERMEDIATES, final judgment adverse to the patentees was rendered Aug. 5, 1982, as to claims 1 and 2.

[*Official Gazette Feb. 1, 1983.*]